United States Patent [19]
Aoki et al.

[11] Patent Number: 5,457,126
[45] Date of Patent: Oct. 10, 1995

[54] USE OF LODOXAMIDE TO TREAT OPHTHALMIC ALLERGIC CONDITIONS

[75] Inventors: K. Roger Aoki; Louis M. DeSantis, both of Fort Worth, Tex.

[73] Assignee: Alcon Laboratories, Inc., Fort Worth, Tex.

[21] Appl. No.: 215,216

[22] Filed: Mar. 21, 1994

Related U.S. Application Data

[63] Continuation of Ser. No. 955,815, Oct. 2, 1992, abandoned, which is a continuation of Ser. No. 734,656, Jul. 23, 1991, abandoned, which is a continuation of Ser. No. 312,434, Feb. 17, 1989, abandoned, which is a continuation of Ser. No. 932,236, Nov. 18, 1986, abandoned.

[51] Int. Cl.$^6$ .................................. A61K 31/275
[52] U.S. Cl. ............................ 514/522; 514/912
[58] Field of Search ........................ 519/552, 912

[56] References Cited

U.S. PATENT DOCUMENTS

| | | | |
|---|---|---|---|
| 3,993,679 | 11/1976 | Hall et al. | 260/465 |
| 4,067,995 | 1/1978 | Wright et al. | 424/304 |
| 4,089,973 | 5/1978 | Hall et al. | 424/304 |
| 4,169,153 | 9/1979 | Wright | 424/304 |
| 4,252,813 | 2/1981 | Wright | 424/263 |
| 4,524,063 | 6/1985 | Wheeler | 424/78 |

OTHER PUBLICATIONS

Aoki, et al., "Topical Anti–Allergic Activity of Lodoxamide Against a Passive Anaphylaxis Reaction in the Rat Conjunctiva", *Investigative Ophthamology and Visual Science,* vol. 26, No. 1 (1985).

Watt, et al., "Protective Effect of Lodoxamide Tromethamine on Allergen Inhalation Challenge", *Journal of Allergy Clinical Immunology,* vol. 66, No. 4, pp. 286–294 (Oct. 1980).

Church, Martin K., "Is inhibition of mast cell mediator release relevant to the clinical activity of anit–allergic drugs?", *Agents and Actions,* vol. 18, No. 3/4, pp. 288–293 (1986).

*Primary Examiner*—Zohreh Fay
*Attorney, Agent, or Firm*—James A. Arno; Gregg C. Brown

[57] ABSTRACT

Disclosed are methods of using certain defined phenylene dioxamic acids in treating allergic ocular responses, such as, hayfever, conjunctivitis, atopic and keratoconjunctivitis, vernal conjunctivitis, giant capillary conjunctivitis and other diseases where mast cell degranulation are important in the etiology, by topical administration of said active to the affected eye; also disclosed are pharmaceutical compositions comprising said actives.

8 Claims, No Drawings

USE OF LODOXAMIDE TO TREAT OPHTHALMIC ALLERGIC CONDITIONS

This is a continuation of application Ser. No. 07/955,815, filed Oct. 2, 1992 now abandoned, which is a continuation of Ser. No. 07/784,656 filed Jul. 23, 1991 (abandoned), which is a continuation of Ser. No. 07/312,434, filed Feb. 17, 1989 (abandoned), which is a continuation of Ser. No. 06/932,236, filed Nov. 18, 1986 (abandoned).

BACKGROUND OF INVENTION

This invention relates to the use of certain phenylene dioxamic acids in treating allergic ocular responses, such as hayfever, conjunctivitis, atopic and keratoconjunctivitis, vernal conjunctivitis, giant capillary conjunctivitis, and other diseases where mast cell degranulation are important in the etiology, by topical administration of said active to the affected eye; also disclosed are pharmaceutical compositions comprising said actives.

Such phenylene dioxamic acids are generically and specifically disclosed, to a representative extent, in U.S. Pat. No. 3,993,679 (issued Nov. 23, 1976), which patent is fully incorporated herein by reference to the extent of defining the subject phenylene dioxamic acids and their synthesis. A species of the defined phenylene dioxamic acid genus of particular interest and of representative value is N-N'-(2-chloro-5-cyano-m-phenylene) dioxamic acid and its pharmaceutically acceptable salts and esters, such as, di-[tris(hydroxymethyl)methylammonium]-N-N'(2-chloro-5-cyano-m-phenylene)dioxamate:

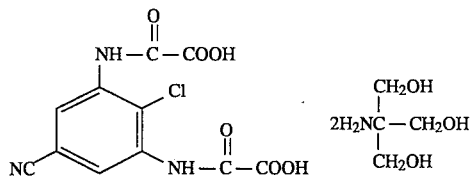

I

The phenylene dioxamic acid of Structure I, above, is known also by the name lodoxamide tromethamine.

The phenylene dioxamic acids of incorporated U.S. Pat. No. 3,993,679 are known to be useful as antiallergics, and, according to the patent disclosure, may be delivered by oral, parenteral, inhalation, rectal means, or by eye drops. The specific salt form of Structure I, above, is disclosed in U.S. Pat. No. 4,524,063 (issued Jun. 18, 1985) to be useful as a topical, ophthalmic antiallergic. However, the patent teaches that to be clinically efficacious the specific lodoxamide salt must be used in a concentration range of from 1–10%, preferably at a level of 5%, in an aqueous vehicle comprising 1–5% polyvinyl alcohol. Such dosage levels are considered quite high—particularly since lodoxamide tromethamine has been reported to cause several types of side effects in a dose related manner. For example, on systemic administration via the oral, intravenous, intrabronchial, or intranasal routes a generalized warming sensation has been reported. Less frequently reported side effects include headaches, nausea, vomiting, nervousness, and the like. The severity and intensity of the side effects decreased with continued usage. The report of such systemic side effects after topical application of an ophthalmic preparation comprising lodoxamide tromethamine has also been reported and is disturbing to the patients and clinicians. Consequently, the therapeutic method and compositions disclosed in the above-cited U.S. Pat. No. 4,524,063 have not been accepted.

Unexpectedly it has been discovered that the phenylene dioxamic acids genus defined by U.S. Pat. No. 3,993,679, which specifically includes lodoxamide and its pharmaceutically acceptable salts and esters including the salt of Structure I, are efficacious for the antiallergic indication when the phenylene dioxamic acid actives are delivered topically by conventional eye drop to the eye at dosage levels under 0.5% concentration when formulated with vehicles of the present invention. In fact, the preferred liquid dosage form for conventional eye drop delivery of the present invention comprises the phenylene dioxamic acid active in the range of 0.1 to 0.25 weight percent. Use of the resulting compositions substantially eliminates occurrence of the aforementioned side effects, and the level of efficacy, quite unlike the teachings of the cited U.S. Pat. No. 4,524,063, is high and acceptable by the ophthalmic clinical community.

DETAILED DESCRIPTION OF INVENTION

The preferred phenylene dioxamic acid of the present invention is lodoxamide and its pharmaceutically acceptable salts and esters. The preferred route of delivery is topically to the eye via an eye dropper from an aqueous solution comprising from about 0.1–0.25 weight percent of the phenylene dioxamic acid active. In the alternative pharmaceutical compositions formulated as ointments or gels can be employed wherein the concentration of the active is in the range of 0.1 to 0.25 weight percent. Such compositions are preferably buffered at a pH of 3.0 to 7.0, preferably pH 5.0. The formulations may also contain preservatives for multi-dose use. While the basic nature of the solution composition is aqueous, agents designed to increase the viscosity may be employed. Such agents as hydroxypropyl methylcellulose, carbopol, polyvinyl alcohol, and the like may be employed. The following formulation is representative.

| Lodoxamide Tromethamine | 0.1 wt. % |
| Sodium Citrate | 0.5 wt. % |
| Citric Acid | 0.21 wt. % |
| Mannitol | 2.29 wt. % |
| Tyloxapol | 0.025 wt. % |
| Disodium Edetate | 0.01 wt. % |
| Benzalkonium Chloride | 0.01% |
| HCl and NaOH | to adjust pH to 5.0 |
| Sterile Pyrogen free Water | Balance |

There are no critical limitations of a technique in compounding the above formulation.

The method of using a formulation of the present invention is left to the routine discretion of the clinician. Typically such formulations are delivered 1–4 times to the affected eye by conventional eye drop device.

What is claimed is:

1. A method of treating ocular allergic responses in a human patient, which comprises applying topically to the affected eye of the human patient a therapeutically effective amount of a composition comprising 0.1 percent by weight of lodoxamide or an equivalent amount of a pharmaceutically acceptable salt or ester of lodoxamide, and a pharmaceutically acceptable vehicle therefor.

2. A method according to claim 1, wherein the composition contains lodoxamide tromethamine.

3. A method according to claim 1, wherein the composition further comprises 0.1 to 0.5 percent by weight of hydroxypropyl methyl cellulose.

4. A method according to claim 1, wherein the composition further comprises an amount of a buffer sufficient to maintain the pH of the composition in the range of 3.0 to 7.0.

5. A method according to claim 4, wherein the buffer comprises sodium citrate and citric acid, and the composition further comprises an amount of mannitol sufficient to provide the composition with an ophthalmically acceptable tonicity and an amount of an ophthalmically acceptable preservative sufficient to maintain the sterility of the composition.

6. A method according to claim 4, wherein the composition contains lodoxamide tromethamine.

7. A method according to claim 1, wherein the composition contains lodoxamide tromethamine and further comprises 0.5 wt. % sodium citrate, 0.21 wt. % citric acid, 2.29 wt. % mannitol, 0.025 wt. % tyloxapol, 0.01 wt. % disodium edetate and 0.01% benzalkonium chloride.

8. A method according to claim 1, wherein the composition is applied topically to the affected eye to treat conjunctivitis.

* * * * *